United States Patent [19]
Boyce et al.

[11] 4,066,770
[45] Jan. 3, 1978

[54] 3-PYRIDYLISOXAZOLIDINE FUNGICIDES

[75] Inventors: Clive B. C. Boyce, Herne Bay; Shirley B. Webb, Faversham, both of England

[73] Assignee: Shell Oil Company, Houston, Tex.

[21] Appl. No.: 717,803

[22] Filed: Aug. 26, 1976

[30] Foreign Application Priority Data
Sept. 2, 1975  United Kingdom ............... 36093/75

[51] Int. Cl.$^2$ ............................................... A01N 9/22

[52] U.S. Cl. ..................................... 424/263; 424/168
[58] Field of Search ...................... 424/263; 260/296 R

[56] References Cited
U.S. PATENT DOCUMENTS 3,849,423  11/1974  Krumkalns et al. ............. 260/296 R Primary Examiner—Dale R. Ore

[57] ABSTRACT

Use as fungicides of certain 3-pyridyl-2-phenylisoxazolidines.

3 Claims, No Drawings

3-PYRIDYLISOXAZOLIDINE FUNGICIDES

DESCRIPTION OF THE INVENTION

It has been found that useful fungicidal properties are possessed by 3-pyridyl-2-phenylisoxazolidines of the general formula

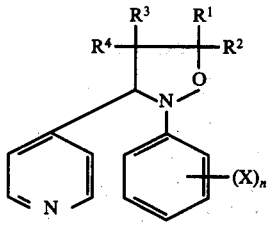

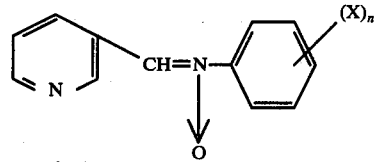

wherein $R^1$ is hydrogen, alkyl or alkenyl; $R^2$ is hydrogen, cyano, alkyl, alkoxy, alkoxycarbonyl, alkanoyloxy, alkylthioalkyl, cyanoalkyl, haloalkyl, hydroxyalkyl, benzyloxyalkyl, or optionally substituted phenyl or phenylthio; $R^3$ is hydrogen or alkyl; $R^4$ is hydrogen, alkyl, alkoxycarbonyl, cyano or optionally substituted phenyl; with the proviso that $R^1$ and $R^3$ together can represent an alkylene moiety of from one to six carbon atoms optionally substituted by alkyl; X is halogen, nitro, cyano, alkyl, alkoxy or phenyl; n is zero, one, two or three.

In these compounds, each alkyl and alkylene moiety preferably contains from one to six carbon atoms and may be of straight-chain or branched-chain configuration; each alkenyl moiety preferably contains from three to six carbon atoms and may be of straight-chain or branched-chain configuration. Any halogen present preferably is chlorine, fluorine or bromine. Where $R^2$ and/or $R^4$ is substituted phenyl, suitable substituents are those moieties represented by X and there may be from one to three of such substituents.

It will be appreciated that these compounds contain at least one asymmetric carbon atom, with three such centres of asymmetry being possible when the substituents $R^1$ and $R^3$ are different from $R^2$ and $R^4$ respectively, and hence these compounds can exist in a number of different geometric and optical isomeric forms. All such geometric and optical isomers, together with physical and racemic mixtures of these isomers, are included within the scope of this invention.

Preferred fungicides are those of Formula I wherein $R^1$ is hydrogen or alkyl of from one to six carbon atoms, $R^2$ is cyano, or is alkoxy or alkanoyloxy wherein the alkyl moiety contains from one to six carbon atoms, phenyl, alkyl of from one to six carbon atoms, optionally substituted by one of chlorine, bromine, alkoxy, alkylthio or benzyloxy; $R^3$ is hydrogen; $R^4$ is hydrogen, cyano or alkyl or alkoxy-carbonyl wherein the alkyl moiety contains from one to six carbon atoms, particularly methyl; n is zero, one or two and X is chlorine or fluorine or alkyl or alkoxy of from one to six carbon atoms.

The isoxazolidines of the invention may be prepared by treating a nitrone of the formula:

with an olefin of the formula:

wherein n, X, $R_1$, $R_2$, $R_3$, $R_4$ have the meanings defined hereinbefore. The nitrone starting material may be prepared by suitable adaptation of known procedures (e.g. as described by Raymond Paul et al., Bulletin de la Societe Chimique de France 1967, pp. 4179–4183). Suitably the reaction can be carried out by refluxing the reactants in an inert solvent, such as benzene, for an appropriate length of time. In certain instances wherein $R^2$ represents a substituted alkyl group, for example an alkylthioalkyl group, the desired compound may most conveniently be prepared by further reacting a 3-pyridyl isozolidine of formula I wherein $R^2$ is, for example, a chloromethyl group.

These isozazolidines have been found to be effective fungicides. Accordingly, this invention provides fungicidal compositions comprising one or more of the compounds defined in Formula I, together with a carrier and optionally a surface-active agent.

The invention also includes a method of protecting crops from attack by fungi, in which crops subject to or subjected to such attack, seeds of such crops or soil in which such crops are growing or are to be grown are treated with a fungicidally effective amount of a composition containing one or more of the componds defined in Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the materials usually applied in formulating pesticides may be used as the carrier.

Suitable solid carriers are natural and synthetic clays and silicates, for example natural silicas such as diatomacious earths; magnesium silicates, for example, talcs; magnesium aluminum silicates, for example, attapulgites and vermiculites; aluminum silicates, for example, kaolinites, montmorillinites or aluminum silicates; elements such as for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilisers, for example superphosphates.

Examples of suitable fluid carriers are water, alcohols, such as for example, isopropanol; glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosine; light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides, fungicides, or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylarly sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols and will generally contain 0.5 to 95% w, preferably 0.5 to 75% w, of toxicant. Wettable powders are usually compounded to contain 25, 50 or 75% w of toxicant and usually contain, in addition to solid carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676 – 0.152 mm), and may be manufactured by agglomeration or impregnation techniques. Generally, granules will contain ½–25% w toxicant and 0–10% w of additives such as stabilisers, slow release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilisers, penetrants and corrosion inhibitors. Suspension concentrates are compounded so as to obtain a stable, non-sedimenting, flowable product and usually contain 10–75% w toxicant, 0.5 – 15% w of dispersing agents, 0.1 – 10% w of suspending agents such as protective colloids and thixotropic agents, 0 – 10% w of appropriate additives such as defoamers, corrosion inhibitors, stabilisers, penetrants and stickers, and as carrier, water or an organic liquid in which the toxicant is substantially insoluble; certain organic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The invention is further illustrated in the following Examples of individual species of the fungicides of the invention, in which the identity of each of the products was confirmed by appropriate chemical and spectral analyses.

EXAMPLE 1

2-phenyl-3-(3'-pyridyl)-5-ethoxyisoxazolidine

A mixture of 59.4 g of 3-pyridyl-N-phenylnitrone and 500 ml of vinyl ethyl ether was stirred and heated under reflux for three days. Excess vinyl ethyl ether was removed using a rotary evaporator, and the residue fractionally distilled to yield 1, as a yellow liquid, b.p. 165°/0.7 Torr.

EXAMPLE 2

2-phenyl-3-(3'-pyridyl)-5-cyanoisoxazolidine

A mixture of 29.7 g of 3-pyridyl-N-phenylnitrone and 15.9 g of acrylonitrile in 300 ml of dry benzene was stirred and heated under reflux for 22 hours. Benzene and excess acrylonitrile were removed in vacuo, and the residue was subjected to column chromatography (neutral alumina/diethyl ether) to yield 2 as a yellow oil.

EXAMPLE 3

2-(p-chlorophenyl)-3-(3'-pyridyl)-5-ethoxyisoxazolidine 11.7 g of 3-pyridyl-N-(p-chlorophenyl)nitrone in 120 ml of benzene was azeotroped to remove water. The solution was cooled to room temperature and a solution of 7.2 g of vinyl ethyl ether in 10 ml of benzene was added. The mixture was stirred and refluxed for 48 hours. The excess ether and benzene were evaporated and the residue was triturated with 60:80 petroluem spirit. The mixture was filtered and the solid was recrystallized from 60:80 petroleum spirit to give 3, as a solid, m.p.: 81°–82.5°.

EXAMPLES 4–15

Following procedures similar to those described in the foregoing Examples, further compounds of the invention were prepared whose physical characteristics are set out in Table I. The structure of these componds is indicated by reference to the substituents in Formula I, $R_3$ and $R_4$ in all cases being hydrogen.

TABLE I

| Ex. | Compound No. | $R_1$ | $R_2$ | n | X | b.p.(Torr.)/ m.p.(° C) |
|---|---|---|---|---|---|---|
| 4  | 4  | H   | —OCOCH$_3$   | 0 | H | 90 – 91° |
| 5  | 5  | CH$_3$ | —C$_2$H$_5$ | 0 | H | 154 – 158(0.6) |
| 6  | 6  | H   | —COOCH$_3$   | 0 | H |  |
| 7  | 7  | H   | —CH$_2$CN    | 0 | H | 124 – 5° |
| 8  | 8  | H   | —CH$_2$Br    | 0 | H |  |
| 9  | 9  | H   | Phenyl       | 0 | H | 69 – 71.5° |
| 10 | 10 | H   | —CH$_2$Cl    | 0 | H |  |
| 11 | 11 | H   | n-C$_4$H$_9$— | 0 | H | 182 – 4(1.0) |
| 12 | 12 | H   | —CH$_2$OH    | 0 | H |  |
| 13 | 13 | H   | —OC$_4$H$_9$(n) | 0 | H |  |
| 14 | 14 | H   | —OC$_2$H$_5$ | 1 | m-Cl |  |
| 15 | 15 | H   | —OC$_2$H$_5$ | 1 | p-OCH$_3$ | 72 – 74° |

EXAMPLE 16

2-phenyl-3-(3'-pyridyl)-5-ethylthiomethyl-isoxazolidine

0.54 g of sodium was dissolved in 25 ml of absolute ethanol. To the stirred solution was added 2 g of ethanethiol, followed by a solution of 6.45 g of 10 prepared following a procedure precisely analogous to that of Example 2, in 25 ml of absolute ethanol. The mixture was stirred and heated under reflux for 2 hours. After cooling, the mixture was filtered, and solvent removed from the filtrate in vacuo. The residue was subjected to column chromatography (neutral alumina/diethyl ether/hexane 1:1) to yield 16 as an oil.

EXAMPLE 17

2-(p-fluorophenyl)-3-(3'-pyridyl)-5-ethoxyisoxazolidine

11.7 g of 3-pyridyl-N-(p-fluorophenyl)nitrone in 120 ml of benzene was azeotroped to remove water, cooled and 7.2 g of vinyl ethyl ether in 10 ml of benzene was added; the mixture was stirred and refluxed for 48 hours. After removal of excess vinyl ethyl ether and benzene the residue was subjected to column chromatography (using a silica gel column and diethyl ether as eluant) followed by recrystallisation from 40:60 petroleum spirit to give 17, as a solid, m.p. 41°–42° C.

EXAMPLE 18

2-(p-chlorophenyl)-3-(3'-pyridyl)-4,5-cyclohexaneisoxazolidine

A mixture of 11.7 g of 3-pyridyl-N-(p-chlorophenyl)-nitrone in 120 ml of xylene and 7.2 g of cyclohexene in 10 ml of xylene was stirred and refluxed for 48 hours. Excess solvent was removed and the residue was subjected to column chromatography (using a silica gel column and diethyl ether as eluent). The eluted product was recrystallised from 60:80 petroleum spirit to give 18, as a solid, m.p. 111°–113° C.

EXAMPLE 19

**Activity against barley powdery mildew (*Erysiphe graminis*)**

The test measured the direct antisporulant activity of compounds applied as a foliar spray. For each compound about 40 barley seedlings were grown to the one-leaf stage in a plastic pot sterile potting compost. Inoculation was effected by dusting the leaves with conidia of *Erysiphe graminis*. 24 hours after inoculation the seedlings were sprayed with a solution of the compound in a mixture of acetone (50%), surfactant (0.054%) and water using a track sprayer. The rate of application was equivalent to 1 kilogram of active material per hectare. First assessment of disease was made 5 days after treatment, when the overall level of sporulation on treated pots were compared with that on control pots.

The extent of disease control is set out in Table II below, expressed as a control rating according to the criteria:-

0 = less than 50% disease control
1 = 50–80% disease control
2 = greater than 80% disease control

TABLE II

| Compound No. | Disease Control | Compound No. | Disease Control |
|---|---|---|---|
| 1 | 2 | 8 | 2 |
| 2 | 2 | 9 | 2 |
| 3 | 2 | 10 | 2 |
| 4 | 2 | 11 | 2 |
| 5 | 2 | 12 | 1 |
| 6 | 1 | 13 | 2 |
| 7 | 1 | 14 | 2 |
|   |   | 15 | 2 |

EXAMPLES 20 – 43

The further individual species of the fungicides of the invention described in Table III were prepared by the procedures described in Examples 1–18. The compounds are identified by structure referring to Formula I. Compounds 20 – 43 were tested as fungicides by the procedure described in Example 19. All were found to have a rating of "2", indicating greater than 80% control of the fungus.

TABLE III

| Ex. No. | Compound No. | $R^3$ | $R^4$ | $R^2$ | $R^1$ | n | X |
|---|---|---|---|---|---|---|---|
| 20 | 20 | H | H | $-OC_2H_5$ | H | 1 | p-OCH$_3$ |
| 21 | 21 | H | H | $-OC_2H_5$ | H | 1 | p-CH$_3$ |
| 22 | 22 | H | CH$_3$OOC— | $-CH_3$ | H | 0 | H |
| 23 | 23 | H | H | $-(CH_2)_5CH_3$ | H | 0 | H |
| 24 | 24 | H | \(-CH_2-\)$_4$- | | H | 0 | H |
| 25 | 25 | H | H | $-SC_6H_5$ | H | 0 | H |
| 26 | 26 | H | H | $-(CH_2)_4CH_3$ | H | 0 | H |
| 27 | 27 | H | H | $-(CH_2)_9CH_3$ | H | 0 | H |
| 28 | 28 | H | $-C_6H_5$ | $-CH_3$ | H | 0 | H |
| 29 | 29 | H | $-CH_3$ | $-C_6H_5$ | H | 0 | H |
| 30 | 30 | H | H | $-C(CH_3)_3$ | H | 0 | H |
| 31 | 31 | H | $-CN$ | $-C_6H_5$ | H | 0 | H |
| 32 | 32 | H | H | $-(CH_2)_4CH_3$ | H | 1 | p-Cl |
| 33 | 33 | H | H | $-(CH_2)_3CH_3$ | H | 1 | p-Cl |
| 34 | 34 | H | \(-CH_2-\)$_4$- | | H | 1 | p-Cl |
| 35 | 35 | H | H | $-OC_2H_5$ | H | 1 | p-F |
| 36 | 36 | H | H | $-OC_2H_5$ | H | 2 | 3,4-Cl$_2$ |
| 37 | 37 | H | H | $-OC_2H_5$ | H | 2 | 3,5-cl$_2$ |
| 38 | 38 | H | H | $-CH_2OCH_2C_6H_5$ | $-CH_3$ | 0 | H |
| 39 | 39 | H | H | -nC$_4$H$_9$ | H | 1 | p-F |
| 40 | 40 | H | \(-CH_2-\)$_4$- | | H | 1 | p-F |
| 41 | 41 | H | H | $-OC_2H_5$ | H | 1 | p-Br |
| 42 | 42 | H | H | $-OC_2H_5$ | H | 2 | 3-Cl,4-F |
| 43 | 43 | H | H | $-OC_2H_5$ | H | 1 | 4-CN |

What is claimed is:

1. A fungicidal composition comprising a carrier, optionally a surface-active agent, and, as active ingredient a fungicidally effective amount of at least one 3-pyridylisoxazolidine of the formula

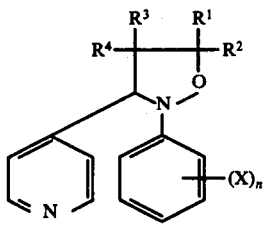

wherein R¹ is hydrogen, alkyl or alkenyl; R² is hydrogen, cyano, alkyl, alkoxy, alkoxycarbonyl, alkanoyloxy, alkylthioalkyl, cyanoalkyl, haloalkyl, hydroxyalkyl, benzyloxyalkyl, or phenyl or phenylthio optionally substituted by from one to three moieties represented by X; R³ is hydrogen or alkyl; R⁴ is hydrogen, alkyl, alkoxycarbonyl, cyano or phenyl optionally substituted by from one to three moieties represented by X; with the proviso that R¹ and R³ together can represent an alkylene moiety of from one to six carbon atoms optionally substituted by alkyl; X is halogen, nitro, cyano, alkyl, alkoxy or phenyl; n is zero, one, two or three, with the further provisos that each alkyl and alkylene moiety contains from one to six carbon atoms; and each alkenyl moiety contains from three to six carbon atoms.

2. A composition according to claim 1 wherein R¹ is hydrogen or alkyl of from one to six carbon atoms, R² is cyano; or is alkoxy or alkanoyloxy wherein the alkyl moiety contains from one to six carbon atoms; phenyl; alkyl or from one to six carbon atoms, optionally substituted by one of chlorine, bromine, alkoxy, alkylthio or benzyloxy; R³ is hydrogen; R⁴ is hydrogen, cyano or alkyl or alkoxycarbonyl wherein the alkyl moiety contains from one to six carbon atoms; n is zero, one or two and X is chlorine or fluorine or alkyl or alkoxy of from one to six carbon atoms.

3. A method of protecting crops from attack by fungi, in which crops subject to or subjected to such attack, seeds of such crops or soil in which such crops are growing or are to be grown are treated with a fungicidally effective amount of a composition according to claim 1.

* * * * *

UNITED STATES PATENT AND TRADEMARK OFFICE
CERTIFICATE OF CORRECTION

PATENT NO. : 4,066,770

DATED : January 3, 1978

INVENTOR(S) : CLIVE B. C. BOYCE and SHIRLEY B. WEBB

It is certified that error appears in the above-identified patent and that said Letters Patent are hereby corrected as shown below:

Column 1, in the formula, change the bond linking the pyridyl ring to the isoxazolidine ring from the carbon atom at the 4-position of the pyridyl ring to the carbon atom at the 3-position of the pyridyl ring.

Claim 1, in the formula, change the bond linking the pyridyl ring to the isoxazolidine ring from the carbon atom at the 4-position of the pyridyl ring to the carbon atom at the 3-position of the pyridyl ring.

Signed and Sealed this

Thirtieth Day of May 1978

[SEAL]

Attest:

RUTH C. MASON
Attesting Officer

LUTRELLE F. PARKER
Acting Commissioner of Patents and Trademarks